United States Patent [19]

Gould et al.

[11] Patent Number: 5,055,109
[45] Date of Patent: Oct. 8, 1991

[54] TORQUE TRANSMITTING ASSEMBLY FOR INTRAVASCULAR DEVICES

[75] Inventors: Ross Gould, Aptos; Isidro Gandionco, Fremont, both of Calif.

[73] Assignee: Advanced Cardiovascular Systems, Inc., Santa Clara, Calif.

[21] Appl. No.: 417,733

[22] Filed: Oct. 5, 1989

[51] Int. Cl.⁵ ............................................. A61M 37/00
[52] U.S. Cl. ..................................... 604/95; 606/194; 128/657
[58] Field of Search .......................... 604/95; 128/4–6, 128/657, 772; 606/194

[56] References Cited

U.S. PATENT DOCUMENTS

| | | | |
|---|---|---|---|
| 3,270,641 | 9/1966 | Gosselin | 128/4 |
| 4,176,662 | 12/1979 | Frazer | 128/6 |
| 4,207,873 | 6/1980 | Kruy | 128/6 |
| 4,277,168 | 7/1981 | Oku | 128/4 |
| 4,619,263 | 10/1986 | Frisbie et al. | 128/772 |
| 4,664,113 | 5/1987 | Frisbie et al. | 128/772 |
| 4,757,827 | 7/1988 | Buchbinder et al. | 128/772 |
| 4,874,371 | 10/1989 | Comben et al. | 604/95 |

FOREIGN PATENT DOCUMENTS

| | | | |
|---|---|---|---|
| 2803897 | 8/1979 | Fed. Rep. of Germany | 128/4 |
| 7631762 | 5/1978 | France | 128/6 |
| 548462 | 10/1942 | United Kingdom | 128/6 |

Primary Examiner—Stephen C. Pellegrino
Assistant Examiner—Ralph A. Lewis
Attorney, Agent, or Firm—Fulwider, Patton, Lee & Utecht

[57] ABSTRACT

A torque transmitting assembly for guidewires, steerable fixed wire catheters and the like with a drive mechanism wherein the rotational output is greater than the rotational input. The assembly has a supporting structure with proximal and distal end pieces and a connecting arm or strut extending between and secured to the end pieces. An outer cylindrical shaped housing is rotatably mounted about the connecting arm and between the ends. A ring gear or other torque transmitting element is secured to the interior of the housing. A pinion gear or other torque transmitting element having a smaller diameter than the ring gear is rotatably mounted within support structure and the housing and is adapted to engage the ring gear in a torque transmitting relationship. The proximal end of a guidewire or the guiding element of a steerable catheter is secured to the pinion gear so that rotation thereof by the rotation of the housing causes a much greater the rotation of the attached guidewire or guiding element. Preferably means are provided to restrict the number of rotations which can be imparted to the guidewire or guiding means.

22 Claims, 3 Drawing Sheets

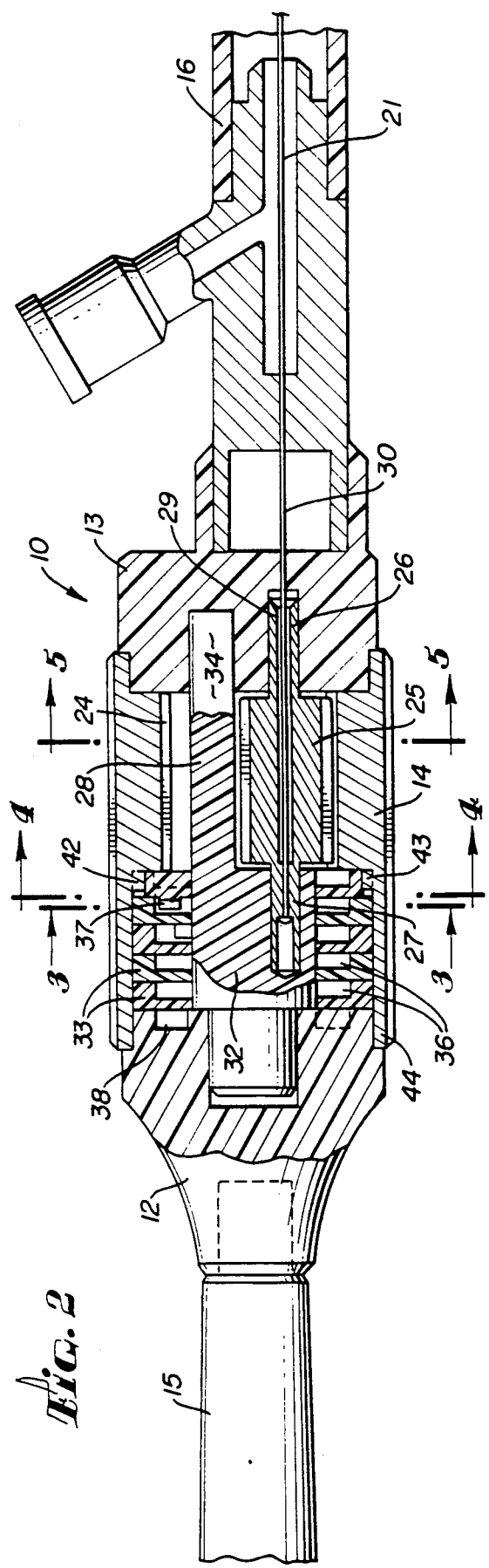
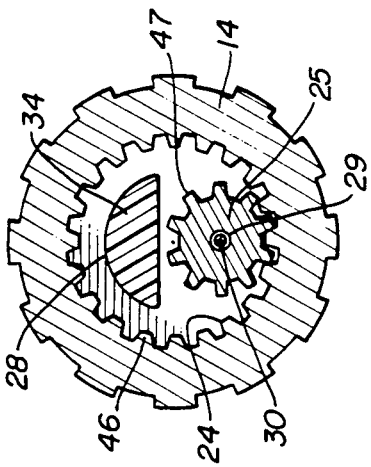
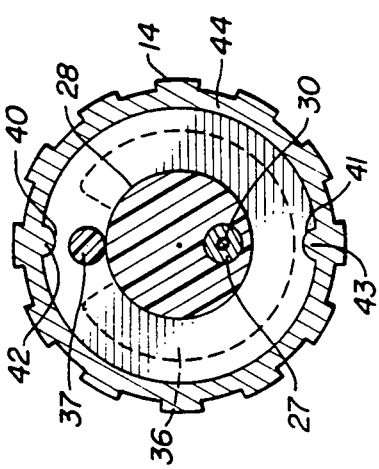
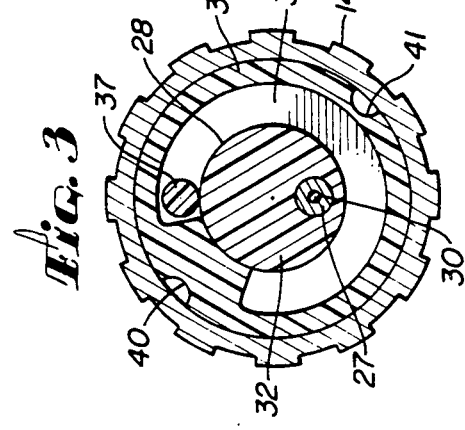

TORQUE TRANSMITTING ASSEMBLY FOR INTRAVASCULAR DEVICES

BACKGROUND OF THE INVENTION

This invention generally relates to torquing devices for guiding members which facilitate the advancement of intravascular catheters in procedures such as percutaneous transluminal coronary angioplasty (PTCA).

In typical PTCA procedures a guiding catheter having a preformed distal tip is percutaneously introduced into the cardiovascular system of a patient and advanced therein until the distal tip thereof is in the coronary artery. A dilatation catheter having an inflatable balloon on the distal portion thereof is advanced into the patient's coronary anatomy through the guiding catheter until the dilatation balloon is properly positioned across the lesion to be dilated. Once in position across the lesion, the balloon is inflated to a predetermined size with radiopaque liquid at relatively high pressures (e.g., greater than 4 atmospheres) to compress the atherosclerotic plaque of the lesion against the inside of the artery wall. The balloon is then deflated so that the dilatation catheter can be removed and blood flow resumed through the dilated artery.

With over-the-wire dilatation catheters, movable guidewire systems, a guidewire is first steered through the coronary anatomy and then the dilatation catheter is advanced over the guidewire until in proper position. With fixed guidewire systems, the guidewire is fixed within the catheter so that both are advanced simultaneously through the patient's coronary arteries.

Steerable dilatation catheters with fixed guiding members provide much smaller deflated profiles than conventional catheters which allows the steerable catheter to cross tighter lesions and to be advanced much deeper into the patient's coronary anatomy. Additionally, procedure time can shorten because there is no need to first advance a guidewire through the stenosis and then advance a conventional dilatation catheter over the previously placed guidewire.

Further details of dilatation catheters, guidewires, and the like for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,538,622 (Samson et al.); U.S. Pat. No. 4,554,929 (Samson et al.); U.S. Pat. No. 4,582,181 (Samson); U.S. Pat. No. 4,616,652 (Simpson) and U.S. Pat. No. 4,638,805 (Powell) which are hereby incorporated herein in their entirety by reference thereto.

Typically, guidewires and guiding elements of steerable catheters have their distal ends shaped or bent by the physician before advancing these devices into the patient's vasculature. The physician then rotates or torques the proximal end of these devices, which extend out of the patient, to cause the shaped distal end to rotate so that the device can be steered to the desired vascular location even in tortuous arterial passageways. During the early periods of PCTA, the proximal end of the guidewire was merely bent into an L shape to allow the physician to more easily rotate the guidewire. It was found, however, that unlimited rotation could twist the balloon so as to interfere with the inflation and/or deflation of the balloon. Torque limiting devices were developed to control the amount of rotation to a predetermined number of rotations of the guidewire and they have met with considerable success. Details of these torquable devices can be found in U.S. Pat. No. 4,619,263 (Frisbie) and U.S. Pat. No. 4, 664,113 (Frisbie), which are hereby incorporated herein in their entirety. These torquing devices, however, were limited to one-to-one rotation between the input to the torquing knob and the output to the guidewire and usually they required both hands of the physician to properly operate which made the procedure very complicated.

What has been needed and heretofore unavailable is a torquing device which provides for a greater rotational output than the rotational input and particularly such a torquing device which could be operated with one hand by the physician who is performing the vascular procedure. The present invention satisfies this need.

SUMMARY OF THE INVENTION

This invention is directed to a torquing assembly for vascular devices such as guidewires, steerable dilatation catheters and the like which have a rotational output greater than the rotational input thereto.

The torquing assembly in accordance with the invention generally includes a support structure having proximal and distal end pieces, a connecting arm or strut extending between the end pieces, and a rotatable housing disposed about the connecting arm and between the end pieces. Fixed within the interior of the rotatable housing is a relatively large diameter driving member, such as a ring gear, and a relatively small diameter driving member such as a pinion gear, which is directly or indirectly engaged in a torque transmitting relationship with the large diameter driving member so that rotation of the housing results in the rotation of the small diameter driving member. The small diameter driving member is preferably provided with a pair of supporting shafts which allows the small diameter driving member to rotate within the housing about an axis which is parallel to the axis of rotation of the housing. One of the shafts is rotatably mounted within a passageway in one of the end pieces with the proximal end of a core member from a guidewire, a steerable dilatation or other intravascular device being secured thereto so that rotation of the small diameter driving members results in the rotation of the core member. The amount of rotation of the small diameter driving member with respect to the rotation of the large diameter driving member is a function of the respective diameters thereof. The effective diameter of the large diameter driving member should be at least 1.5 times the effective diameter of the small diameter driving member, preferably about 2 to 4 times as great.

The torquing device of the invention should be provided with means to limit the number of turns which may be applied to the core member secured to the small diameter driving member. A particularly suitable means is disclosed in U.S. Pat. No. 4,664,113 which involves a plurality of discs adjacent to one another on a common axis, with each of the discs having a projection on one side and an arcuate annular recess or guideway on the other side which is adapted to receive the projection of the adjacent disc. The rotation of a disc about its axis causes the projection on the opposite side to travel around the arcuate recess in the adjacent disc until it comes to the end of the arcuate pathway. Each disc generally represents less than one rotation of the rotational member secured thereto which in the presently preferred embodiment is the large diameter driving member.

The distal end piece is preferably provided with an elongated handle so that the torquing assembly can be held in and operated with a single hand. The handle can be gripped within the palm of the operator's hand and the rotatable housing can be rotated by the operator's thumb and forefinger to rotate the core member secured to the small diameter driving member therein.

The torquing assembly of the invention is very effective in rotating core members in a wide variety of intravascular devices, including steerable dilatation catheters and guidewires. The rotational output of the assembly can be readily adjusted by changing the diameter of the small diameter drive member. By including a rotation limiting device, the operator can be assured that the core member is being rotated only within certain safe limits. For example, if the intravascular device is a dilatation catheter, the balloon will not be overly wrapped so as to interfere with the inflation or deflation thereof. Additionally, it is now well known that over rotation can also stress the core member or components thereon beyond safe limits so that catastrophic failure can occur. For example in some instances, the coiled tip on the distal end of a guidewire or fixed wire catheter can fall off within a patient's coronary artery if torqued excessively.

These and other advantages of the invention will become more apparent from the following detailed description thereof when taken in conjunction with the accompanying exemplary drawings.

BRIEF DESCRIPTION OF THE DRAWINGS

FIG. 2 is an enlarged longitudinal cross-sectional view of the torquing assembly shown in FIG. 1;

FIG. 3 is a transverse cross-sectional view taken along the lines 3—3 shown in FIG. 2;

FIG. 4 is a transverse cross-sectional view taken along the lines 4—4 shown in FIG. 2;

FIG. 5 is a transverse cross-sectional view taken along the lines 5—5 shown in FIG. 2.

DETAILED DESCRIPTION OF THE INVENTION

Figure 1:
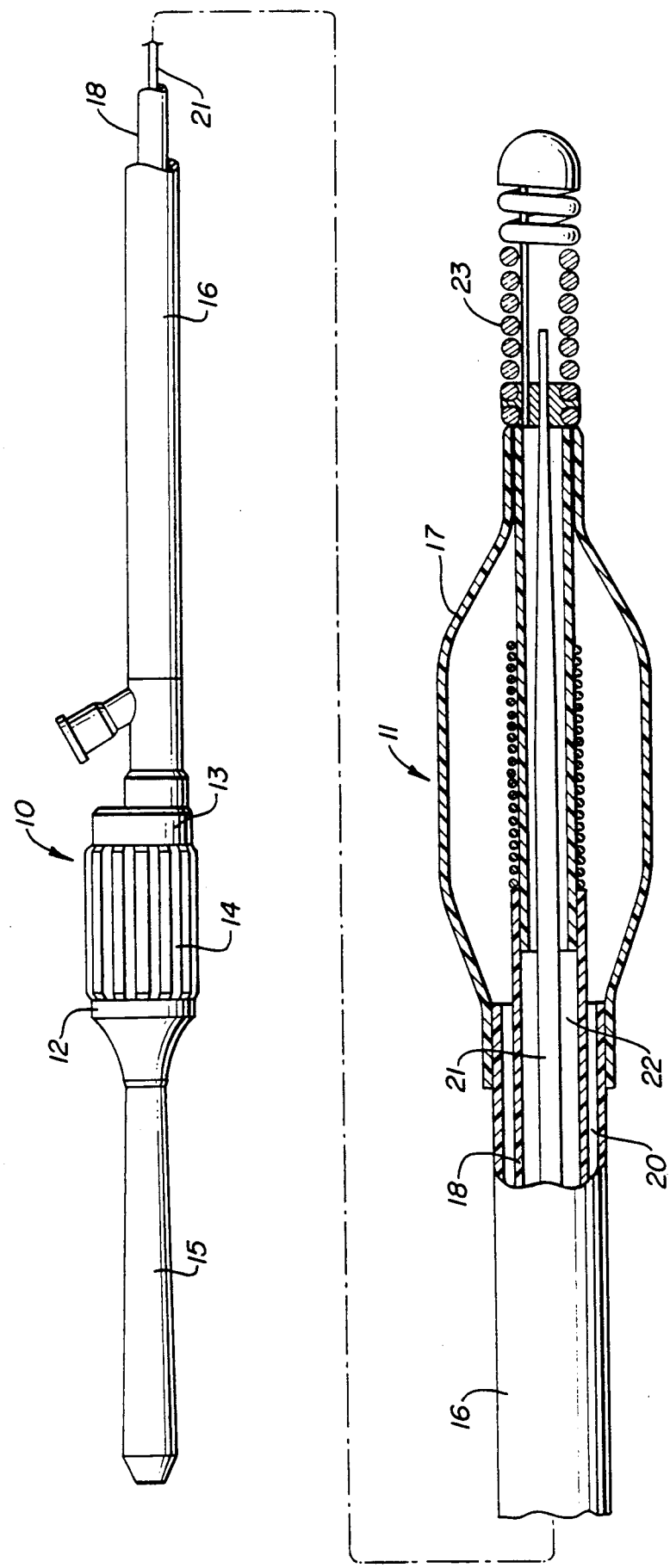
FIG. 1 is an elevational view partially in section of a torquing assembly embodying features of the invention which is attached to a steerable fixed wire dilatation catheter.

FIG. 1 illustrates a torquing assembly 10 which embodies features of the invention connected to the proximal end of a fixed wire, steerable dilatation catheter 11. The assembly 10 generally includes a proximal end piece 12, a distal end piece 13, a rotatable housing 14 disposed between the end pieces and a handle 15 secured to the proximal end piece 12.

The catheter 11 generally includes an outer tubular member 16 to which a flexible relatively inelastic balloon 17 is secured to the distal end thereof. An inner tubular member 18 is disposed within the outer tubular member 16 and defines an annular inflation lumen 20 for directing inflation fluid to the interior of the balloon 17. Core member 21 extends through the inner lumen 22 of inner tubular member 18, through the interior of balloon 17 and out the distal end thereof with a flexible coil 23 disposed about and secured to the portion of the core member 21 which extends out the distal end of the balloon. Further details of the catheter 11 can be found in copending application Ser. No. 287,772 filed Dec. 21, 1988, which is hereby incorporated by reference in its entirety.

FIG. 2 shows in more detail the interior working parts of the torquing assembly 10. A ring gear 24 is secured within the interior of rotatable housing 14. Preferably, both the ring gear and housing are made as a single unitary piece. A pinion gear 25 is disposed within the ring gear 24 and is in a torque transmitting relationship therewith. It is supported within the ring gear 24 by shafts 26 and 27 which are seated in recesses provided in the distal end piece 13 and in arm piece 28. An inner lumen 29 extends through shafts 26 and 27 and the pinion gear 25 which is adapted to receive the proximal end 30 of the core member 21 which is fixed therein by adhesive or other suitable means so that rotation of pinion gear 25 results in the torquing of the core member 21.

As illustrated shown in FIGS. 2-4, the end pieces 12 and 13 are held together by strut or arm piece 28 which extends through the interior of the ring gear 24. The proximal portion 32 of the arm piece 28 has a cylindrical shape and receives a plurality of rotation limiting discs 33. The arm piece 28 is provided with an extension 34 on the proximal end thereof which fits within a recess provided in the proximal end piece 12.

Figure 6:
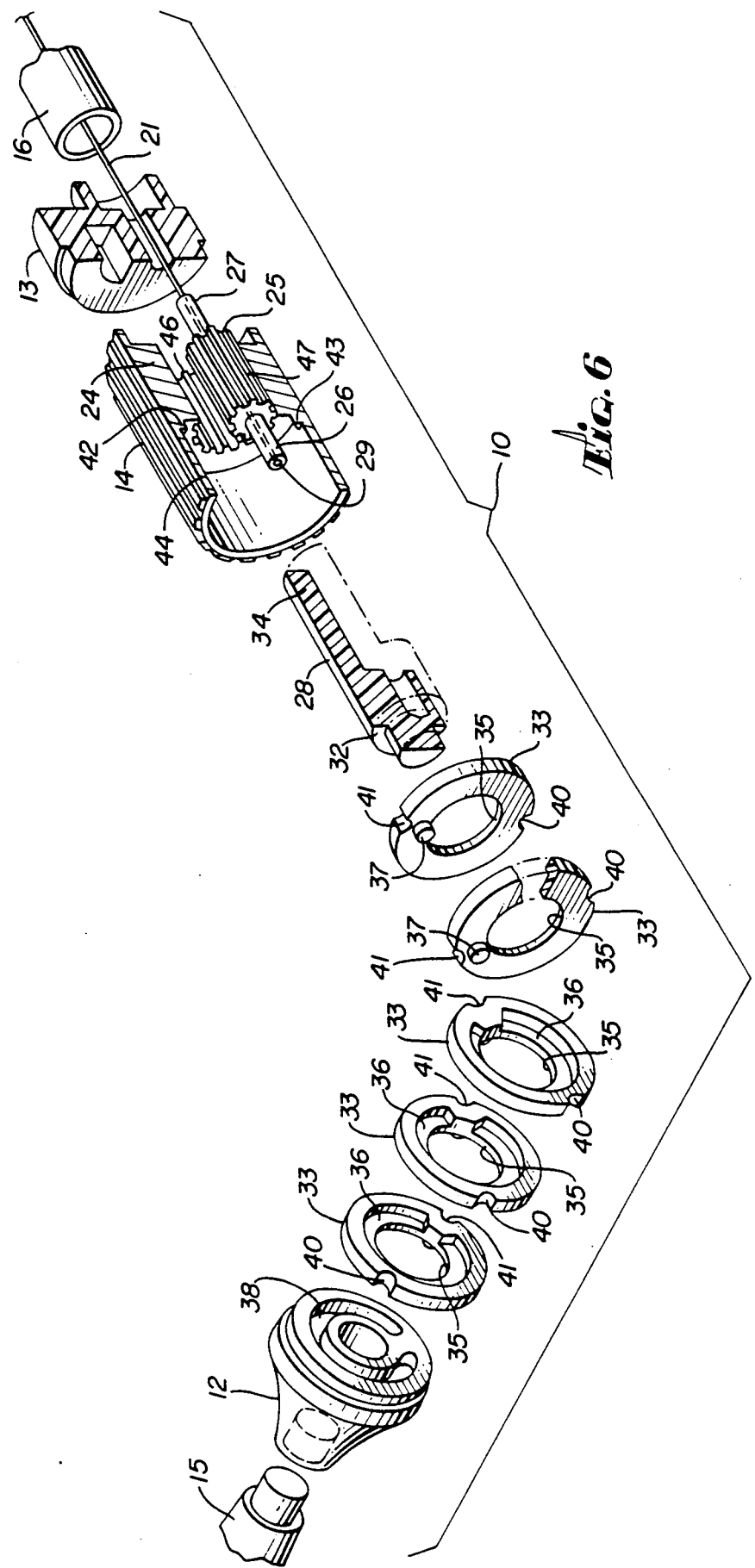
FIG. 6 is an exploded perspective view partially in section of the torquing assembly shown in FIGS. 1-5 wherein part of the assembly is rotated at an angle of 90° with respect to the remainder of the assembly to illustrate the opposite sides of the elements thereof.

As shown more clearly in FIG. 6, the rotation limiting discs 33 generally have a central aperture 35 which allows the discs to slide over and rotate about the rounded proximal portion 32 of the arm piece 28. An arcuate recess 36 is provided on the distal side thereof which is adapted to receive the projection 37 on the proximal side of an adjacent disc. The inner face of the proximal end piece 13 is also provided with a similar arcuate recess or guidewire 38 as in the discs 33 which receives the projection 35 on the most proximal of the discs.

The most distal of the discs 33 has a pair of semi-circular recesses 40 and 41 in the outer periphery thereof which are adapted to receive the ridges 42 and 43, respectively, provided on the interior of the cylindrical extension 44 of the rotatable housing 14 to thereby fix the most distal disc 33 with respect to the housing extension 44. Rotation of the housing 14 and the ring gear 24 thereby causes the rotation of the most distal disc 33 about the cylindrical end 32 of arm 28. The projection 37 on the proximal side of the most distal disc 33 follows the arcuate guideway 36 in the distal face of the adjacent disc. When projection 37 engages the end of the arcuate guideway, it causes the rotation of the adjacent disc about the end 32 of the arm 28 until the projection 37 on the adjacent disc reaches an end of the arcuate guideway on yet another adjacent disc. The rotation of the remaining discs 33 occurs in essentially the same manner. The proximal end piece 12 is provided with an arcuate recess or guideway 45 in the distal face thereof, which is essentially the same as the arcuate guideway 36 in the distal faces of the discs 33 which receives the projection 37 on the most proximal of the discs 33. When the projection 37 on this most proximal disc reaches the end of the arcuate guideway 38 in the end piece 12, the rotation of the housing and the ring gear with respect to the proximal end piece 12 is terminated in that direction.

The diameters of the ring gear 24 and the pinion gear 25 as well as the number and size of the teeth 46 and 47 thereof, respectively, can be varied to suit the needs of the particular vascular device in which the torque transmitting assembly is utilized. Generally the effective diameter of the ring gear 24 is at least 1.5 times larger than the effective diameter of the ring gear so as to increase the rotational output of the assembly 10 over the rotational input. Preferably, the ring gear has a diameter from about 2 to about 4 times the effective diameter of the pinion gear to provide a rotational output of between about 2 and 4 times the rotational input.

The gears are usually made of metal with the pinion gear 25 preferably made of brass and the ring gear 24 and the housing 14 made of aluminum. However, other materials are contemplated, such as nylon and other suitable plastic materials which have been used for various types of torque transmitting devices.

The end pieces 12 and 13, the support arm 28 and the discs 33 may be made from a wide variety of suitable polymer materials but they are preferably formed from a polycarbonate.

To operate the torquing assembly 10, it is placed in the palm of the operator's hand so that the operator's thumb and index finger can easily engage the rotatable housing 14. Rotation of the housing 14 and the ring gear 24 fixed thereto causes the rotation of the pinion gear 25 and the core member 21 of the guidewire or fixed wire steerable catheter which is secured to the distal shaft 27 of the pinion gear. The torque applied to the core member 21 is transmitted to the distal tip of the guidewire or catheter.

While the torquing member of the present invention is described herein in conjunction with a guidewire or a steerable fixed wire catheter for angioplasty procedures, it will be appreciated by those skilled in the art that the torquing member is suitable for use with a wide variety of intravascular devices.

What is claimed is:

1. A torque transmitting assembly for intravascular devices having elongated catheter bodies with flexible members on the distal end thereof, comprising:
   a) a support structure including proximal and distal end pieces and a connecting arm having proximal and distal ends secured to the proximal and distal end pieces respectively;
   b) a cylindrically shaped housing rotatably mounted on the support structure about the connecting arm between the end pieces thereof;
   c) a first rotatable drive means disposed within the interior of the housing and fixed thereto;
   d) a second rotatable drive means which is rotatably mounted within the housing in a torque transmitting relationship with the first drive means, which has a smaller diameter than the first drive means and which has proximal and distal shafts, with at least one of the proximal or distal shafts being rotatably mounted within one of the end pieces of the support structure; and
   e) a rotatable shaft secured to the second drive member so that the rotational output thereof is greater than the rotational input imparted to the first drive member.

2. The torque transmitting assembly of claim 1 wherein the first drive means is a ring gear and the second drive means is a pinion gear.

3. The torque transmitting assembly of claim 1 including means to limit the number of rotations imparted to the rotatable shaft secured to the second drive means.

4. The torque transmitting assembly of claim 3 wherein the means to limit the rotation of the shaft secured to the second drive means includes a plurality of interfitting circular discs which have an arcuate guideway in one face thereof and a projection on the opposite face thereof which extends into the arcuate guideway in an adjacent disc.

5. The torque transmitting assembly of claim 4 wherein one of the ends of the supporting structure is provided with an inner face having an arcuate guideway adapted to receive a projection from an adjacent disc.

6. The torque transmitting assembly of claim 4 wherein at least one of the end discs is provided with a recess in the periphery thereof which is adapted to receive a stopping member secured to an element of the supporting structure and be immobilized thereby.

7. The torque transmitting device of claim 4 wherein the supporting structure is provided with a cylindrical portion about which the discs are rotatably mounted.

8. The torque transmitting assembly of claim 1 wherein an elongated handle is provided on the proximal end piece of the support structure which facilitates holding the assembly in the palm of the operator's hand.

9. The torque transmitting assembly of claim 1 wherein the first drive means has a diameter which is at least 1.5 times larger than the diameter of the second drive means so that one rotation of the first drive means effects at least 1.5 rotations of the second drive means.

10. The torque transmitting assembly of claim 9 wherein the first drive means has an effective diameter of between 2 and 5 times that of the second drive means so that one rotation of the first drive means effects between about 2 and about 5 rotations of the second drive means.

11. The torque transmitting assembly of claim 1 wherein the first drive means directly engages the second drive means.

12. The torque transmitting assembly of claim 1 wherein an elongated core member of a guiding member is secured to a shaft fixed to the second drive means.

13. The torque transmitting assembly of claim 1 wherein the ring gear and the pinion gear are made of metallic materials.

14. A method of applying a torque to an intravascular guiding member having an elongated core member, comprising:
   a) fixing to the proximal end of the elongated core member a torque transmitting assembly comprising:
      i) a support structure including proximal and distal end pieces and a connecting arm having proximal and distal ends secured to the proximal and distal end pieces respectively,
      ii) a cylindrically shaped housing rotatably mounted on the support structure about the connecting arm between the end pieces thereof,
      iii) a first rotatable drive means disposed within the interior of the housing and fixed thereto,
      iv) a second rotatable drive means which is rotatably mounted within the housing in a torque transmitting relationship with the first drive means, which has a smaller diameter than the first drive means and which has proximal and distal shafts, with at least one of the proximal or distal shafts being rotatably mounted within one of the end pieces of the support structure, and v) a rotatable shaft secured to the second drive means so that the rotational output thereof is greater than the rotational input imparted to the first drive means, b) rotating the housing and the first drive means fixed thereto so as to rotate the second drive means and the proximal end of the core member fixed thereto; and c) the core member transmitting the torque applied thereto to the distal end of the guide member.

15. An intravascular device including an elongated, torque transmitting shaft which has proximal and distal ends, a flexible element secured to the distal end thereof and a torque transmitting assembly secured to the proximal end thereof, the torque transmitting assembly comprising:

a) a support structure including proximal and distal end pieces and a connecting arm having proximal and distal ends secured to the proximal and distal end pieces respectively;

b) a cylindrically shaped housing rotatably mounted on the support structure about the connecting arm between the end pieces thereof;

c) a first rotatable drive means disposed within the interior of the housing and fixed thereto;

d) a second rotatable drive means which is rotatably mounted within the housing in a torque transmitting relationship with the first drive means, which has a smaller diameter than the first drive means and which is fixed at one end thereof to the elongated shaft and which is fixed on the other end thereof to a second shaft which is rotatably mounted within one of the end pieces of the support structure, the rotational output of the second rotational drive means being greater than the rotational input imparted to the first rotational drive means.

16. The intravascular device of claim 15 wherein the first rotational drive means is a ring gear and the second rotational drive means is a pinion gear.

17. The intravascular device of claim 15 including means to limit the number of rotations imparted to the elongated rotatable shaft secured to the second drive means.

18. The intravascular device of claim 15 wherein an elongated handle is provided on the proximal end piece of the support structure which facilitates holding the assembly in the palm of the operator's hand.

19. The intravascular device of claim 15 wherein the first drive means has a diameter which is at least 1.5 times larger than the diameter of the second drive means so that one rotation of the first drive means effects at least 1.5 rotations of the second drive means.

20. The intravascular device of claim 15 wherein the first drive means has an effective diameter of between 2 and 5 times that of the second drive means so that one rotation of the first drive means effects between about 2 and about 5 rotations of the second 21. The intravascular device of claim 15 wherein the first drive means directly engages the second drive means.

22. The intravascular device of claim 15 wherein means are provided to limit the rotation of the elongated shaft secured to the second rotational drive means including a plurality of interfitting circular discs which have an arcuate guideway in one face thereof and a projection on the opposite face thereof which extends into the arcuate guideway in an adjacent disc.

* * * * *